: US008906213B2

United States Patent
Sasaki (10) Patent No.: US 8,906,213 B2
(45) Date of Patent: Dec. 9, 2014

(54) NOX SENSOR CONTROL APPARATUS (75) Inventor: Hisashi Sasaki, Konan (JP)

(73) Assignee: NGK Spark Plug Co., Ltd., Aichi (JP)

( * ) Notice: Subject to any disclaimer, the term of this patent is extended or adjusted under 35 U.S.C. 154(b) by 525 days.

(21) Appl. No.: 13/365,520

(22) Filed: Feb. 3, 2012

(65) Prior Publication Data

US 2012/0199478 A1 Aug. 9, 2012

(30) Foreign Application Priority Data

Feb. 4, 2011 (JP) ................ 2011-022349

(51) Int. Cl.
*G01N 27/407* (2006.01)
*G01N 27/41* (2006.01)
*G01N 27/419* (2006.01)

(52) U.S. Cl.
CPC ........ *G01N 27/419* (2013.01); *F01N 2560/026* (2013.01); *F01N 2560/20* (2013.01)
USPC ...................................... 204/426

(58) Field of Classification Search
CPC  G01N 27/4067; G01N 27/4071; G01N 27/41
See application file for complete search history.

(56) References Cited

U.S. PATENT DOCUMENTS 6,214,207 B1   4/2001  Miyata et al.
2009/0051373 A1* 2/2009  Kato et al. ................ 324/693

FOREIGN PATENT DOCUMENTS

JP         10-142194 A       5/1998

* cited by examiner

*Primary Examiner* — Alex Noguerola
(74) *Attorney, Agent, or Firm* — Sughrue Mion, PLLC (57) ABSTRACT

In a NOx sensor control apparatus (1), a NOx sensor includes a heater (164), and an oxygen concentration detection cell (130), a first pumping cell (110) and a second pumping cell (120) which are arranged sequentially in the axis O direction. The NOx sensor control apparatus 1 includes a first impedance detection means (59a, 60) which detects the first impedance of the first cell (oxygen concentration detection cell), a heater control means (60) which performs an energization control of a heater such that the first impedance becomes a target value, a second impedance detection means (59b, 60) which detects the second impedance of the second cell (second pumping cell), and an output correction means (60) which corrects an output of at least the third cell (first pumping cell) based on the deviation between the first impedance and the second impedance.

3 Claims, 8 Drawing Sheets

| INCLINATION (TEMPERATURE GRADIENT COEFFICIENT) Kd | TEMPERATURE COMPENSATION QUANTITY Tco |
|---|---|
| Kd1 | Tco1 |
| Kd2 | Tco2 |

NOX SENSOR CONTROL APPARATUS

TECHNICAL FIELD

The present invention relates to a NOx sensor control apparatus connected to a NOx sensor which has three cells each of which includes a solid electrolyte and a pair of electrodes and also has a heater.

BACKGROUND ART

As a gas sensor for performing the enhancement of fuel economy and combustion control of an internal combustion engine of an automobile or the like, there has been known an oxygen sensor or an air/fuel sensor which detects the oxygen concentration in an exhaust gas. Further, along with the strengthening of the regulations on an exhaust gas from an automobile, there has been a demand for the reduction of an amount of nitrogen oxide (NOx) in the exhaust gas, and a NOx sensor which can directly measure the concentration of NOx has been developed.

As such a NOx sensor, there has been known a sensor which includes a NOx sensor element having three cells each of which includes a pair of electrodes formed on a surface of oxygen-ion conductive solid electrolyte made of zirconia or the like. The NOx sensor element extends in the axial direction, and is constituted of a first pumping cell, an oxygen concentration detection cell and a second pumping cell arranged sequentially from a distal end side as viewed along the axial direction, and the periphery of the NOx sensor element is held by a body fitting.

A first measuring chamber into which a gas to be measured is introduced is defined in the NOx sensor, and the first pumping cell is arranged so as to face the first measuring chamber. By performing an energization control of the first pumping cell by a sensor control apparatus to which the NOx sensor is connected, the first pumping cell is driven so as to pump out oxygen from the first measuring chamber or to pump oxygen into the first measuring chamber from the outside. The oxygen concentration detection cell is provided in such a manner that the oxygen concentration detection cell is laminated to the first pumping cell and faces the first measuring chamber. A voltage (electric motive force) corresponding to the oxygen concentration in the first measuring chamber is outputted by the oxygen concentration detection cell. The energization control of the first pumping cell is performed such that the voltage outputted by the oxygen concentration detection cell becomes a predetermined voltage, and the oxygen concentration in a gas to be measured in the first measuring chamber is controlled to the predetermined concentration by driving the first pumping cell. Here, an electric current which flows in the first pumping cell is correlated with the oxygen concentration in the gas to be measured and hence, the oxygen concentration in the gas to be measured can be detected based on the electric current.

Then, the gas to be measured whose oxygen concentration is controlled flows into a NOx measuring chamber (second measuring chamber) which is communicated with the first measuring chamber. By applying a fixed voltage to the second pumping cell which faces the NOx measuring chamber, NOx in the gas to be measured is decomposed so that an electric current corresponding to the NOx concentration flows between a pair of electrodes of the second pumping cell whereby the NOx concentration can be detected based on this electric current.

Here, to accurately detect the oxygen concentration and the NOx concentration, it is necessary to activate each cell by heating the NOx sensor to a predetermined activation temperature (for example, a predetermined temperature of 750° C. or above) and hence, a heater is provided to the NOx sensor as an integral part of each cell, and the NOx sensor is connected to a control apparatus which performs an energization control of the heater. With respect to such a NOx sensor control apparatus, there has been developed a technique where impedance (inner resistance) of one cell which constitutes a NOx sensor is measured and an energization state of the heater is controlled such that measured impedance becomes preset target impedance (see patent document 1). Usually, the NOx sensor control apparatus, while performing such a control of the energization state of the heater, performs a control of an energization state of each cell, and also converts an electric current which flows into the second pumping cell into a voltage, calculating a detection value of NOx concentration (concentration converted value) based on the voltage, and outputting the detected value to an external engine control apparatus.

RELATED ART DOCUMENTS

Patent Documents

[Patent Document 1] JP-A-10-142194

SUMMARY OF THE INVENTION

Problems to be Solved by the Invention

As described above, in the prior art, the energization control of the heater is performed such that a temperature of one cell which constitutes the NOx sensor element becomes a fixed value. However, the NOx sensor element is elongated in the axial direction, and three cells are sequentially arranged along the axial direction and hence, a temperature gradient takes place between the respective cells. Further, when a distal end side of the element is rapidly cooled due to a flow speed of an exhaust gas or the like or when a temperature of the body fitting of the NOx sensor mounted on an exhaust pipe changes, the degree of this temperature gradient also changes. That is, even when the energization control of the heater is performed based on impedance measured by one cell, there arises a case where the temperature gradient between the respective cells of the NOx sensor element changes due to a change in use environment. Due to this change in temperature gradient, an error occurs in an output of the cell thus giving rise to a drawback that the accuracy in detecting oxygen concentration or NOx concentration is lowered.

That is, it is an object of the present invention to provide a NOx sensor control apparatus which enhances accuracy in detecting oxygen concentration or NOx concentration by compensating for a change in an output of a cell caused by a change in a temperature gradient of a NOx sensor element in the axial direction.

Means for Solving the Problems

To overcome the above-mentioned drawbacks, the NOx sensor control apparatus according to the present invention is a NOx sensor control apparatus which is connected to a NOx sensor, the NOx sensor having a NOx sensor element which includes: an oxygen concentration detection cell which has an oxygen ion conductive solid electrolyte and a pair of electrodes, and generates an output corresponding to oxygen concentration in a gas to be measured which is introduced into a first measuring chamber; a first pumping cell which has an oxygen ion conductive solid electrolyte and a pair of electrodes, adjusts oxygen concentration in the first measuring chamber by pumping out or pumping in oxygen in the gas to be measured which is introduced into the first measuring chamber such that the output of the oxygen concentration detection cell becomes a predetermined value, and allows an output corresponding to the oxygen concentration in the gas to be measured; a second pumping cell which has an oxygen ion conductive solid electrolyte and a pair of electrodes, and allows a pumping current corresponding to NOx concentration in the gas to be measured which flows into the NOx measuring chamber from the first measuring chamber and has oxygen concentration thereof adjusted to flow therein; and a heater, the first pumping cell, the oxygen concentration detection cell and the second pumping cell are sequentially arranged from a distal end side along the axial direction of the NOx sensor element, wherein the NOx sensor control apparatus includes: a first impedance detection means which detects first impedance of a first cell which is constituted of one of the oxygen concentration detection cell, the first pumping cell and the second pumping cell; a heater control means which performs an energization control of the heater such that the first impedance of the first cell becomes a target value; a second impedance detection means which detects second impedance of a second cell which is constituted of one of the oxygen concentration detection cell, the first pumping cell and the second pumping cell, and differs from the first cell; and an output correction means which corrects at least an output of a third cell which differs from the first cell and the second cell based on the deviation between the first impedance and the second impedance.

The NOx sensor element is elongated in the axial direction and three cells are sequentially arranged along the axial direction and hence, a temperature gradient is generated between the respective cells, and this temperature gradient is also changed due to a change in a use environment. Accordingly, in the present invention, an output of the third cell is corrected for performing the temperature compensation by estimating a temperature of the third cell based on the deviation between the first impedance and the second impedance expressing temperature gradient between the first cell and the second cell. In the present invention, in correcting the output of the third cell, while the deviation between the impedance of the first cell and the impedance of the second cell is used, the energization control of the heater is performed by the heater control means such that the impedance of the first cell becomes the target value. Accordingly, the impedance of the first cell which is one of the cells for acquiring the deviation indicates the value approximately near the target value and hence, the value of deviation becomes a value which accurately expresses the degree of the temperature gradient of the NOx sensor element. Further, in the present invention, the correction of the output of the third cell is performed based on this deviation and hence, an error in the output of the third cell caused by a change in the temperature gradient can be eliminated or reduced whereby the accuracy in the detection of the concentration of a specific gas can be enhanced. Still further, in performing the correction of the output of the third cell, it is unnecessary to detect impedances of three cells and hence, it is possible to provide the NOx sensor control apparatus which can enhance the accuracy in the detection of the concentration of a specific gas without making the circuit constitution complicated.

When the third cell is constituted of the first pumping cell, the accuracy in the detection of the oxygen concentration in a gas to be measured can be enhanced by applying the present invention, while when the third cell is constituted of the second pumping cell, the accuracy of the detection of concentration of NOx can be enhanced by applying the present invention. Further, when the third cell is constituted of the oxygen concentration detection cell, the adjustment of the oxygen concentration by driving the first pumping cell becomes stable and hence, the accuracy in the detection of the concentration of NOx can be enhanced.

Still further, in the present invention, at least the output of the third cell is corrected using the deviation between the first impedance and the second impedance, and the output of the second cell may be corrected using this deviation. With respect to the second cell, the second impedance is detected and hence, the output of the second cell may be corrected based on the second impedance.

Still further, with respect to the correction of the output of the third cell by the output correction means, the output of the third cell may be corrected directly using the above-mentioned deviation by a suitable technique. However, by calculating the temperature gradient coefficient between the first cell and the second cell using the above-mentioned deviation and by correcting the output of the third cell using the temperature gradient coefficient, the correction of the output of the third cell can be realized with high accuracy.

The first cell may preferably be the oxygen concentration detection cell.

When the first cell is the oxygen concentration detection cell, the impedance of the first cell indicates a value approximately near the target value by means of the heater control means and hence, the accuracy of the output of the oxygen concentration detection cell becomes stable. Accordingly, driving of the first pumping cell based on the output of the oxygen concentration detection cell becomes accurate and hence, the oxygen concentration in the gas to be measured which flows into the NOx measuring chamber from the first measuring chamber becomes approximately fixed whereby the accuracy in the detection of the concentration of NOx based on an electric current which flows into the second pumping cell can be enhanced.

Advantageous Effect of the Invention

According to the present invention, a change in an output of a cell due to a temperature gradient of a NOx sensor element in the axial direction can be compensated and hence, the accuracy of the detection of oxygen concentration or NOx concentration can be enhanced.

MODES FOR CARRYING OUT THE INVENTION

An embodiment of the present invention is explained hereinafter.

Figure 1:
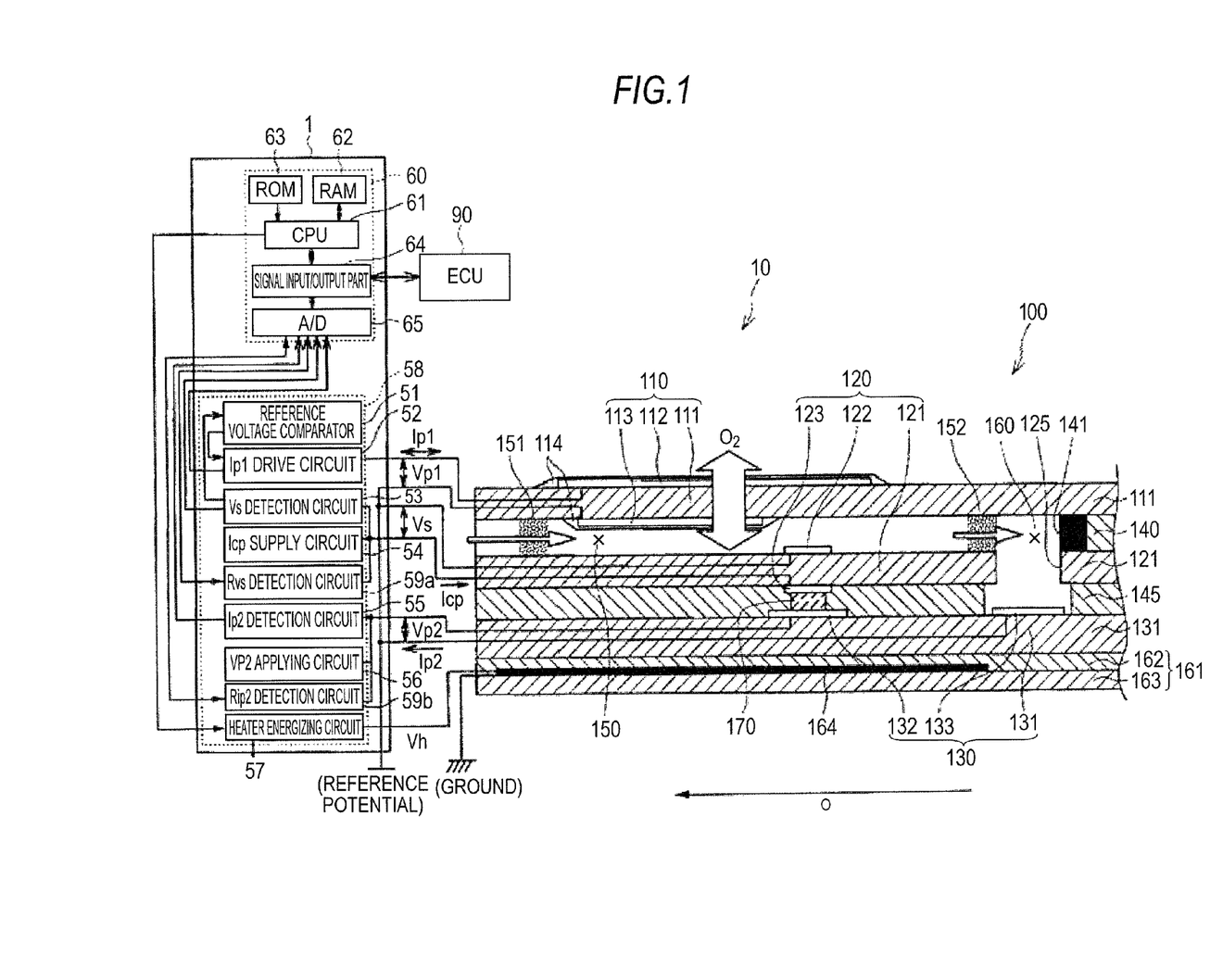
FIG. 1 is a block diagram showing the constitution of a NOx sensor control apparatus according to an embodiment of the present invention.

FIG. 1 is a block diagram showing the constitution of a NOx sensor control apparatus (controller) 1 according to the embodiment of the present invention. The NOx sensor control apparatus 1 is mounted on a vehicle which is provided with an internal combustion engine (hereinafter also referred to as "engine") not shown in the drawing. The NOx sensor control apparatus 1 is electrically connected to a connector (not shown in the drawing) which a NOx sensor 10 includes, and the NOx sensor control apparatus 1 is also electrically connected to a vehicle-side control apparatus (ECU 90).

The NOx sensor control apparatus 1 calculates a detection value (concentration converted value) of oxygen concentration in a gas to be measured and a detection value (concentration converted value) of NOx concentration in the gas to be measured respectively based on a signal outputted from the NOx sensor 10, outputs the detection values to the ECU 90 respectively, and the ECU 90 executes processing such as a control of an operation state of the engine, purification of NOx accumulated in a catalyst or the detection of abnormality in the catalyst corresponding to the oxygen concentration or the NOx concentration.

The NOx sensor control apparatus 1 is provided with a control circuit 58 and a microcomputer (micon) 60 on a printed circuit board (not shown in the drawing) housed in a casing. The microcomputer 60 controls the whole NOx sensor control apparatus 1, and includes a CPU (central processing unit) 61, a RAM 62, a ROM 63, a signal input/output part 64, an A/D converter 65 and clocks not shown in the drawing, and a program which is prestored in the ROM or the like is executed by the CPU.

The control circuit 58 includes a reference voltage comparator 51, an Ip1 drive circuit 52, a Vs detection circuit 53, an Icp supply circuit 54, an Ip2 detection circuit 55, a Vp2 applying circuit 56, a heater energizing circuit 57, an Rvs detection circuit 59a, and an Rip2 detection circuit 59b. The control circuit 58 controls a NOx sensor element 100, and also detects a first pumping current and a second pumping current which flow into the NOx sensor element 100 and outputs these electric currents to the microcomputer 60.

Next, the constitution of the NOx sensor 10 (NOx sensor element 100) is explained. The Nox sensor 10 is of a type where the NOx sensor element 100 having an elongated plate shape which extends in an axis O direction is housed in a predetermined housing and the NOx sensor 10 also includes connection terminals and lead lines for connection with the NOx sensor control apparatus 1. Since the constitution of the sensor and the housing per se is known, the NOx sensor element 100 is explained in conjunction with a cross-sectional view 1 taken along the axis O direction hereinafter.

The NOx sensor element 100 has the structure where a first solid electrolytic layer 111, an insulation layer 140, a second solid electrolytic layer 121, an insulation layer 145, a third solid electrolytic layer 131 and insulation layers 162, 163 are laminated in this order. A hollow first measuring chamber 150 is defined between the first solid electrolytic layer 111 and the second solid electrolytic layer 121 and a gas to be measured is introduced into the first measuring chamber 150 from the outside by way of a porous first diffusion resistance body 151 arranged on a left end (inlet) of the first measuring chamber 150.

A second diffusion resistance body 152 is arranged on an end of the first measuring chamber 150 opposite to the inlet, and a hollow NOx measuring chamber 160 which is communicated with the first measuring chamber 150 is defined on a right side of the first measuring chamber 150 by way of the second diffusion resistance body 152. The NOx measuring chamber 160 penetrates the second solid electrolytic layer 121 and is formed between the first solid electrolytic layer 111 and the third solid electrolytic layer 131.

A heater 164 having an elongated plate shape which extends along the longitudinal direction of the NOx sensor element 100 is embedded between the insulation layers 162, 163. The heater 164 is used for elevating a temperature of the NOx sensor element 100 to a target temperature for activation. Due to the elevation of the temperature of the NOx sensor element 100, conductivity of oxygen ion in the respective solid electrolytic layers 111, 121, 131 is enhanced so that an operation of the NOx sensor element 100 is stabilized. Further, as described later, an energization control of the heater 164 is performed at a predetermined cycle for holding the temperature of the NOx sensor element 100 (NOx sensor 10) at an approximately fixed temperature against a sharp change in an ambient temperature.

Insulation layers 140, 145 are mainly made of alumina, and the first diffusion resistance body 151 and the second diffusion resistance body 152 are made of a porous material such as alumina. The heater 164 is made of platinum or the like.

A first pumping cell 110 includes the first solid electrolytic layer 111 mainly made of zirconia having oxygen ion conductivity, and an inner first pumping electrode 113 and a first counter electrode 112 which constitutes a counter electrode for the inner first pumping electrode 113 which are arranged so as to sandwich the first solid electrolytic layer 111 therebetween, and the inner first pumping electrode 113 faces the first measuring chamber 150. Both the inner first pumping electrode 113 and the first counter electrode 112 are mainly made of platinum, and surfaces of the respective electrodes are covered with a protective layer 114 formed of a porous body respectively.

An oxygen concentration detection cell 120 includes the second solid electrolytic layer 121 mainly made of zirconia, and a detection electrode 122 and a reference electrode 123 which are arranged so as to sandwich the second solid electrolytic layer 121, and the detection electrode 122 faces the first measuring chamber 150 downstream of the inner first pumping electrode 113. Both the detection electrode 122 and the reference electrode 123 are mainly made of platinum.

The insulation layer 145 is cut away such that the reference electrode 123 which is in contact with the second solid electrolytic layer 121 is arranged in the inside of the insulation layer 145, and the cutout portion is filled with a porous body thus forming a reference oxygen chamber 170. By preliminarily supplying an extremely low electric current Icp of a fixed value to the oxygen concentration detection cell 120 using the Icp supply circuit 54, oxygen is supplied to the inside of the reference oxygen chamber 170 from the first measuring chamber 150 thus controlling an atmosphere in the reference oxygen chamber 170 to an oxygen atmosphere which becomes a reference.

A second pumping cell 130 includes the third solid electrolytic layer 131 mainly made of zirconia, and an inner second pumping electrode 133 arranged on a surface of the third solid electrolytic layer 131 which faces the NOx measuring chamber 160 and a second counter electrode 132 which constitutes a counter electrode for the inner second pumping electrode 133. Both the inner second pumping electrode 133 and the second counter electrode 132 are mainly made of platinum.

The second counter electrode 132 is arranged in the cutout portion of the insulation layer 145 above the third solid electrolytic layer 131, and faces the reference oxygen chamber 170 while being arranged opposite to the reference electrode 123.

The inner first pumping electrode 113, the detection electrode 122, and the inner second pumping electrode 133 are connected to a reference potential respectively. The first counter electrode 112 is connected to the Ip1 drive circuit 52, and the reference electrode 123 is connected to the Vs detection circuit 53, the Icp supply circuit 54 and the Rvs detection circuit 59a in parallel. The second counter electrode 132 is connected to the Ip2 detection circuit 55 and the Vp2 applying circuit 56 in parallel. The heater energization circuit 57 is connected to the heater 164.

Here, the first pumping cell 110, the oxygen concentration detection cell 120 and the second pumping cell 130 are arranged in this order from a distal end side of the NOx sensor element 100 along the axis O direction. Further, since the NOx sensor element 100 is elongated in the axis O direction, it is difficult for the heater 164 to make all cells consisting of the first pumping cell 110, the oxygen concentration detection cell 120, and the second pumping cell 130 hold the target temperature. Accordingly, the heater 164 is controlled so as to the manage the temperature of one of these cells (the oxygen concentration detection cell 120 in this embodiment) at a target temperature.

Accordingly, in this embodiment, the oxygen concentration detection cell 120 corresponds to "first cell" in Claims. In this embodiment, the second pumping cell 130 corresponds to "second cell" in Claims, and the first pumping cell 110 corresponds to "third cell" in Claims.

The respective circuits in the control circuit 58 have following functions.

The Ip1 drive circuit 52 supplies a first pumping current Ip1 between the inner first pumping electrode 113 and the first counter electrode 112, and detects the first pumping current Ip1 during the supply of the first pumping current Ip1. The Vs detection circuit 53 detects a voltage (electric motive force) Vs between the detection electrode 122 and the reference electrode 123, and outputs a detection result to the reference voltage comparator 51.

The reference voltage comparator 51 compares a reference voltage (for example, 425 mV) and an output of the Vs detection circuit 53, and outputs a comparison results to the Ip1 drive circuit 52. Further, the Ip1 drive circuit 52 controls the magnitude and the current supply direction of the first pumping current Ip1 such that the voltage Vs becomes equal to the above-mentioned reference voltage thus adjusting the oxygen concentration in the first measuring chamber 150 to predetermined low oxygen concentration.

The Icp supply circuit 54 supplies extremely low electric current Icp between the detection electrode 122 and the reference electrode 123 thus feeding oxygen to the inside of the reference oxygen chamber 170 from the first measuring chamber 150.

The Vp2 applying circuit 56 applies a fixed voltage Vp2 (for example, 450 mV) of the degree by which NOx (to be more specific, NO) in a gas to be measured is decomposed into oxygen and N2 between the inner second pumping electrode 133 and the second counter electrode 132 thus decomposing NOx into nitrogen and oxygen.

The Ip2 detection circuit 55 detects the second pumping current Ip2 which flows into the second pumping cell 130 (between the inner second pumping electrode 133 and the second counter electrode 132) in the form that the current is converted into a voltage such that oxygen generated by the decomposition of NOx is pumped out from the NOx measuring chamber 160.

The Ip1 drive circuit 52 outputs a value of the first pumping current Ip1 detected by the Ip1 drive circuit 52 per se to the A/D converter 65 in the form that the first pumping current Ip1 is converted into a voltage. Further, the Ip2 detection circuit 55 outputs a value of the second pumping current Ip2 detected by the Ip2 drive circuit 55 per se to the A/D converter 65 in the form that the second pumping current Ip2 is converted into a voltage.

The A/D converter 65 converts these values into digital values, and outputs the digital values to the CPU 61 via the signal input/output part 64.

The Rvs detection circuit 59a performs a control of supplying a constant current to the oxygen concentration detection cell 120 in response to an instruction from the micon 60 or stopping the supply of the constant current for every predetermined timing, and outputs a voltage change amount of the oxygen concentration detection cell 120 when the constant current is supplied to the micon 60 (A/D converter 65).

The Rip2 detection circuit 59b performs a control of supplying a fixed pulse-like voltage to the second pumping cell 130 in response to an instruction from the micon 60 or stopping the supply of the fixed pulse-like voltage for every predetermined timing, and outputs a current change quantity of the second pumping cell 130 when the pulse-like voltage is supplied to the micon 60.

Here, the inner resistances (impedances) of the respective cells 120, 130 of the gas sensor element depend on temperatures of the respective cells 120, 130 and hence, the temperatures of the respective cells 120, 130 can be measured by detecting these impedances. Then, values of the impedances of the respective cells 120, 130 are calculated based on output change amounts of the respective cells 120, 130 and the above-mentioned currents or voltages supplied to the respective cells 120, 130, and the temperatures of the respective cells 120, 130 are calculated based on the relationship between the values of the impedances and the temperatures of the respective cells 120, 130 (for example, a map).

The Rvs detection circuit 59a and the microcomputer 60 (the CPU 61 of the microcomputer 60) correspond to "first impedance detection means" in Claims, and the Rip2 detection circuit 59b and the microcomputer 60 (the CPU 61 of the microcomputer 60) correspond to "second impedance detection means" in Claims. Further, the impedance of the oxygen concentration detection cell 120 corresponds to "first impedance" in Claims, and the impedance of the second pumping cell 130 corresponds to "second impedance" in Claims.

Next, one example of the control of the NOx sensor 10 using the control circuit 58 is explained. Firstly, when an engine is started and electricity is supplied to the NOx sensor 10 from an external power source, the heater 164 is operated via the heater energizing circuit 57 so that the first pumping cell 110, the oxygen concentration detection cell 120 and the second pumping cell 130 are heated to an activation temperature (target temperature). The Icp supply circuit 54 supplies an extremely low current Icp between the detection electrode 122 and the reference electrode 123 whereby oxygen is supplied to the reference oxygen chamber 170 from the first measuring chamber 150.

Then, when the respective cells 110 to 130 are heated to the activation temperature, to allow the oxygen concentration in the first measuring chamber 150 to take the predetermined low oxygen concentration, the first pumping cell 110 pumps out oxygen in a gas to be measured (exhaust gas) which flows into the first measuring chamber 150 toward the first counter electrode 112 from the inner first pumping electrode 113 or pumps in oxygen toward the inner first pumping electrode 113 from the first counter electrode 112 side by a feedback control which uses an output of the oxygen concentration detection cell 120. Here, the linear relationship is established between an electric current Ip1 which flows into the first pumping cell 110 and the oxygen concentration and hence, the oxygen concentration in a gas to be measured can be detected due to the detection of the first pumping current Ip1 by the Ip drive circuit 52.

A gas to be measured whose oxygen concentration is adjusted further flows toward the NOx measuring chamber 160 from the first measuring chamber 150. Then, the Vp2 applying circuit 56 applies, as inter-electrode voltage (inter-terminal voltage) of the second pumping cell 130, a fixed voltage Vp2 (for example, 450 mV) of the degree by which a NOx gas in a gas to be measured is decomposed into oxygen and $N_2$ gas thus decomposing NOx into nitrogen and oxygen. Then, a second pumping current Ip2 flows into the second pumping cell 130 so that the second pumping cell 130 pumps out oxygen generated by the decomposition of NOx from the NOx measuring chamber 160. Here, the linear relationship is established between the second pumping current Ip2 and the NOx concentration and hence, the NOx concentration in a gas to be measured can be detected due to the detection of the second pumping current Ip2 by the Ip2 detection circuit 55.

Next, the energization control of the heater 164 using the Rvs detection circuit 59a and the heater energizing circuit 57 is explained. The heater energizing circuit 57 and the microcomputer 60 (the CPU 61 of the microcomputer 60) correspond to "heater control means" in Claims.

Firstly, the CPU 61 calculates impedance Rpvs of the oxygen concentration detection cell 120 based on a voltage change amount (differential voltage) measured by the Rvs detection circuit 59a, and executes an energization control of the heater 164 such that the impedance Rpvs becomes a target value. Accordingly, the oxygen concentration detection cell 120 is substantially held at the target temperature.

The energization control processing of the heater 164 can be performed by a PWM control (PWM energization) which calculates a duty ratio for energizing the heater 164, for example, such that the impedance Rpvs becomes the target value.

Next, the temperature compensation processing which is the technical feature of the present invention and is provided for correcting outputs of the first pumping cell 110 and the second pumping cell 130 is explained. Since the temperature compensation processing is performed by the micon 60, the micon 60 corresponds to "output correction means" in Claims.

Figure 2:
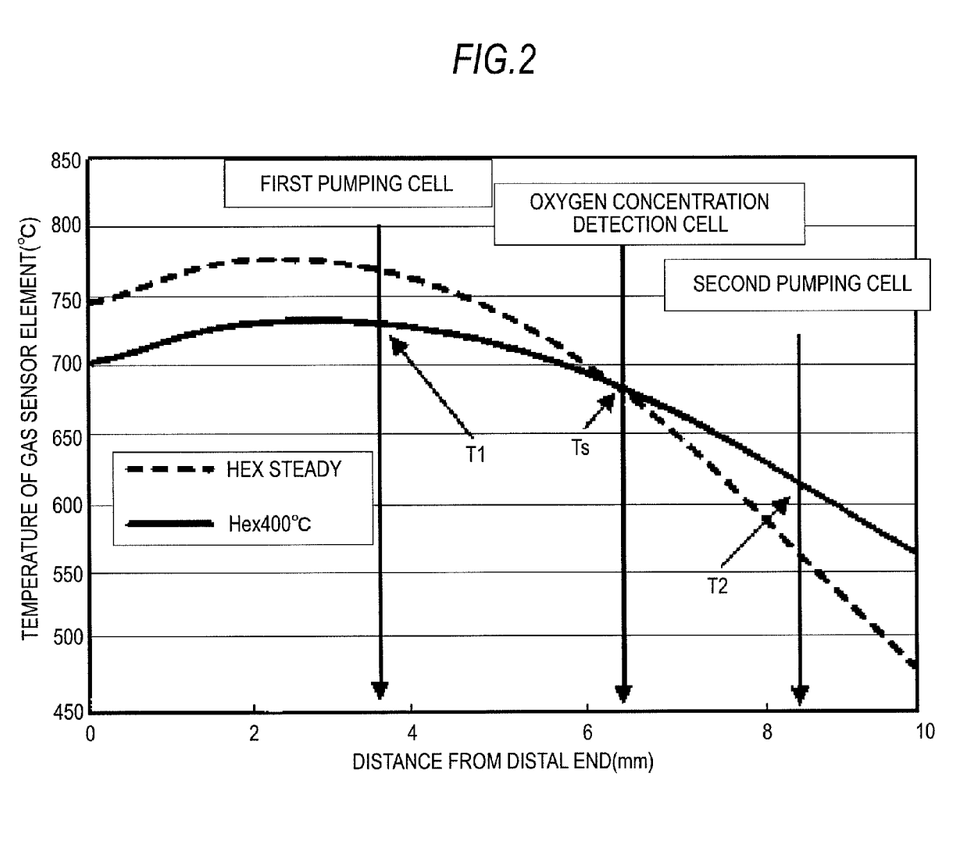
FIG. 2 is a view showing the temperature distribution in the axial direction of a NOx sensor element when a temperature of a body fitting which holds the NOx sensor element is changed.

Firstly, the concept of the temperature compensation processing is explained based on FIG. 2. In FIG. 2, two curves indicate the temperature distributions of the NOx sensor element 100 in the axis O direction when a temperature of a body fitting which holds the NOx sensor element 100 is changed to 400° C. and a steady temperature (150° C.) respectively. The NOx sensor element 100 is elongated in the axis O direction and hence, a temperature gradient where a temperature is gradually lowered toward the second pumping cell 130 from the first pumping cell 110 along the axis O direction takes place. Further, it is understood that when a temperature of the body fitting (that is, a temperature of an outer portion of the gas sensor) changes, heat quantity transferred to the body fitting from the NOx sensor element 100 also changes so that the degree of temperature gradient also changes.

Here, a temperature of the oxygen concentration detection cell 120 is controlled using a heater such that the temperature of the oxygen concentration detection cell 120 becomes a fixed temperature. Accordingly, even when the temperature of the body fitting changes, the cell temperature Ts is held at a substantially fixed level and the respective curves intersect with each other at a position (cell temperature Ts) of the oxygen concentration detection cell 120. Further, the cell temperature of the first pumping cell 110 and the cell temperature of the second pumping cell 130 are set to T1, T2 respectively. In the present invention, it is necessary that the target temperature of one cell (first cell) is controlled by the heater 164. This is because with no cell where the value of the temperature (impedance) is approximately fixed in FIG. 2 and FIG. 3, when the deviation between the impedance of the first cell and the impedance of the second cell is obtained, it becomes impossible to accurately grasp a change in the temperature gradient.

Figure 3:
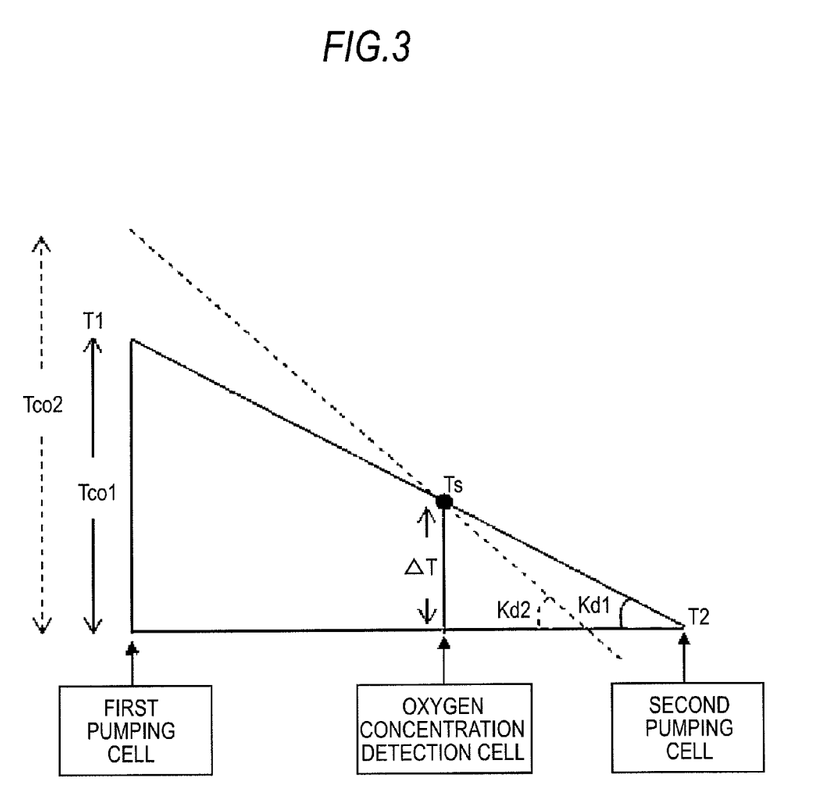
FIG. 3 is a view showing a method of estimating a temperature of a first pumping cell based on a temperature gradient between an oxygen concentration detection cell and a second pumping cell.

As shown in FIG. 3, the temperature of the first pumping cell 110 can be estimated using an extrapolation based on the temperature gradient coefficient Kd by detecting the impedances of the first cell and the second cell (the oxygen concentration detection cell 120 and the second pumping cell 130 in this embodiment) respectively, by obtaining a temperature gradient coefficient Kd between the cells 120, 130 (Kd1, Kd2 corresponding to the respective curves in FIG. 2 respectively) using the deviation between these impedances, and by approximating that the remaining third cell (the first pumping cell 110 in this embodiment) is positioned on a straight line having the same temperature gradient coefficient Kd. To be more specific, the temperatures Ts, T2 of the respective cells 120, 130 are obtained based on the impedances of the respective cells 120, 130, and the inclination of the straight line (temperature gradient coefficient)$Kd(=(Ts-T2)/\Delta Xs2)$ is calculated. Here, $\Delta Xs2$ is a distance in the axis O direction between the oxygen concentration detection cell 120 and the second pumping cell 130 (to be more specific, a distance in the axis O direction from a center position of a length of the detection electrode 122 of the oxygen concentration detection cell 120 to a center position of a length of the inner second pumping electrode 133 of the second pumping cell 130 in the axis O direction). Then, a temperature compensation quantity $Tco(=T1-Ts)$ of the first pumping cell 110 can be obtained from a distance $\Delta Xs1$ in the axis O direction between the oxygen concentration detection cell 120 and the first pumping cell 110 (to be more specific, a distance in the axis O direction from a center position of a length of the detection electrode 122 of the oxygen concentration detection cell 120 to a center position of a length of the inner first pumping electrode 113 of the first pumping cell 110 in the axis O direction) and the temperature gradient coefficient Kd. Although this method does not accurately reflect the above-mentioned curves, calculation processing can be simply performed with ease.

Figure 4:
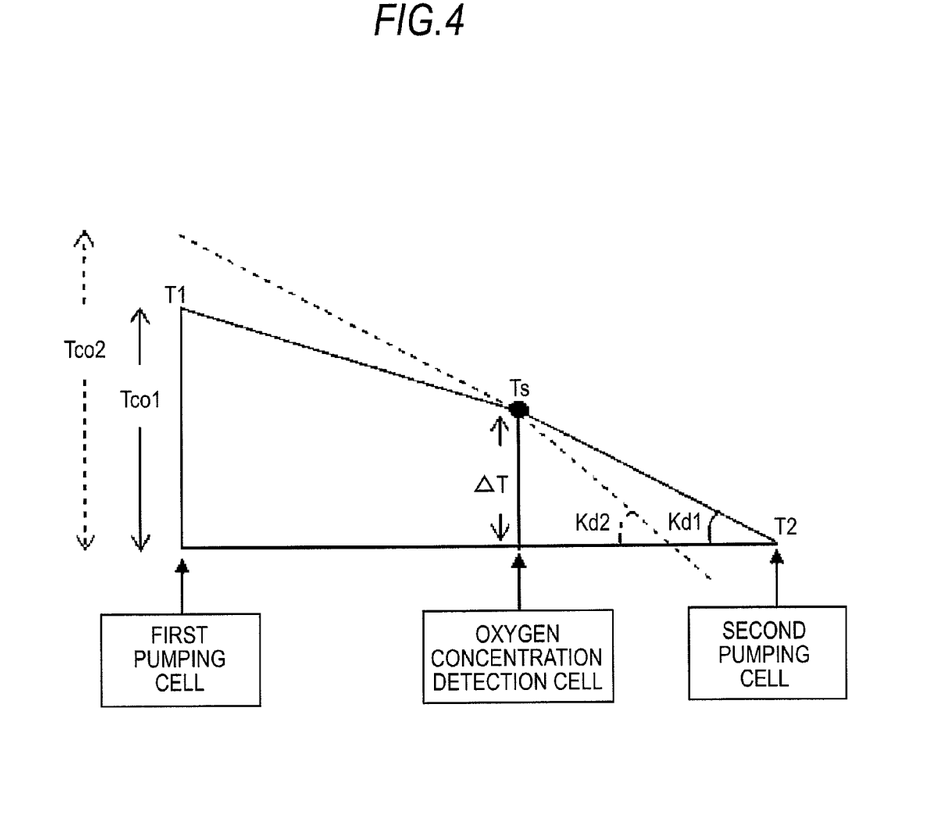
FIG. 4 is another view showing a method of estimating a temperature of the first pumping cell based on a temperature gradient between the oxygen concentration detection cell and the second pumping cell.

On the other hand, when the accurate reflection of the relationship among Ts, T1, T2 by the curves shown in FIG. 2 is required, the curves shown in FIG. 2 when an external temperature of the NOx sensor element is changed are prepared in large number in advance. Then, as shown in FIG. 4, the temperature gradient coefficient Kd between the respective cells 120, 130 is obtained based on the cell temperatures Ts, T2, and a value of the temperature compensation quantity Tco at this point of time is set as an actually measured value read from the curves shown in FIG. 2. Then, the actually measured values of Tco are stored in a table (map) in a state where the actually measured values of Tco are correlated with the respective temperature gradient coefficients Kd and, at the time of performing temperature compensation processing, the temperature compensation quantity Tco is referenced from the table after calculation of the temperature gradient coefficient Kd.

Figure 5:
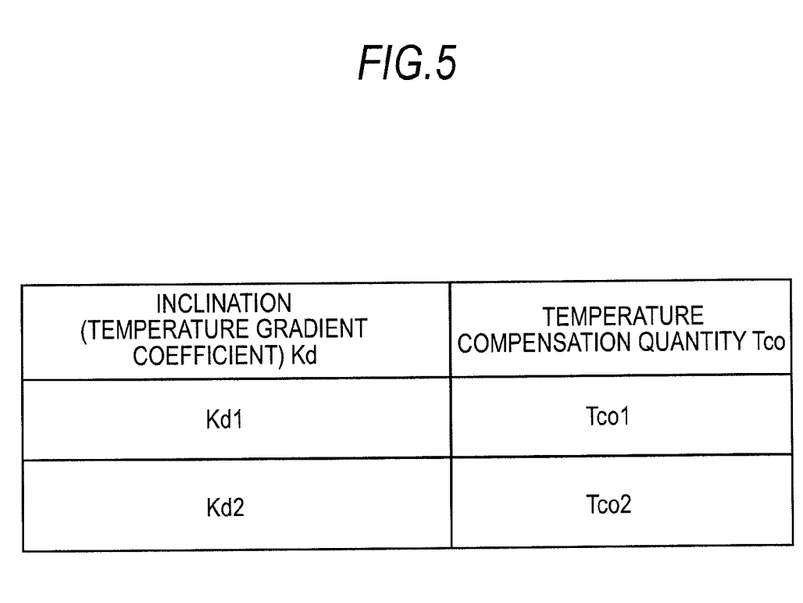
FIG. 5 is a view showing a table indicating the relationship between Kd and Tco.

FIG. 5 is a table showing the relationship between the temperature gradient coefficient Kd and the temperature compensation quantity Tco. The table can be stored in the ROM 63. To be more specific, in the table, the respective relationships between the temperature gradient coefficient Kd and the temperature compensation quantity Tco when the temperature of the NOx sensor element is variously changed (the temperature compensation quantity Tco1 for the temperature gradient coefficient Kd1 when the temperature of the body fitting is 400° C. (solid line in FIG. 3), and the temperature compensation quantity Tco2 for the temperature gradient coefficient Kd2 when the temperature of the body fitting is a steady temperature (150° C. (broken line in FIG. 3)) are stored. Although FIG. 5 shows the table which indicates the relationship between two temperature gradient coefficients Kd and the temperature compensation quantity Tco for facilitating the understanding of the present invention, it is needless to say that a table which indicates the relationship between three or more temperature gradient coefficients Kd and the temperature compensation quantity Tco is applicable to perform the temperature compensation with higher accuracy.

Figure 6:
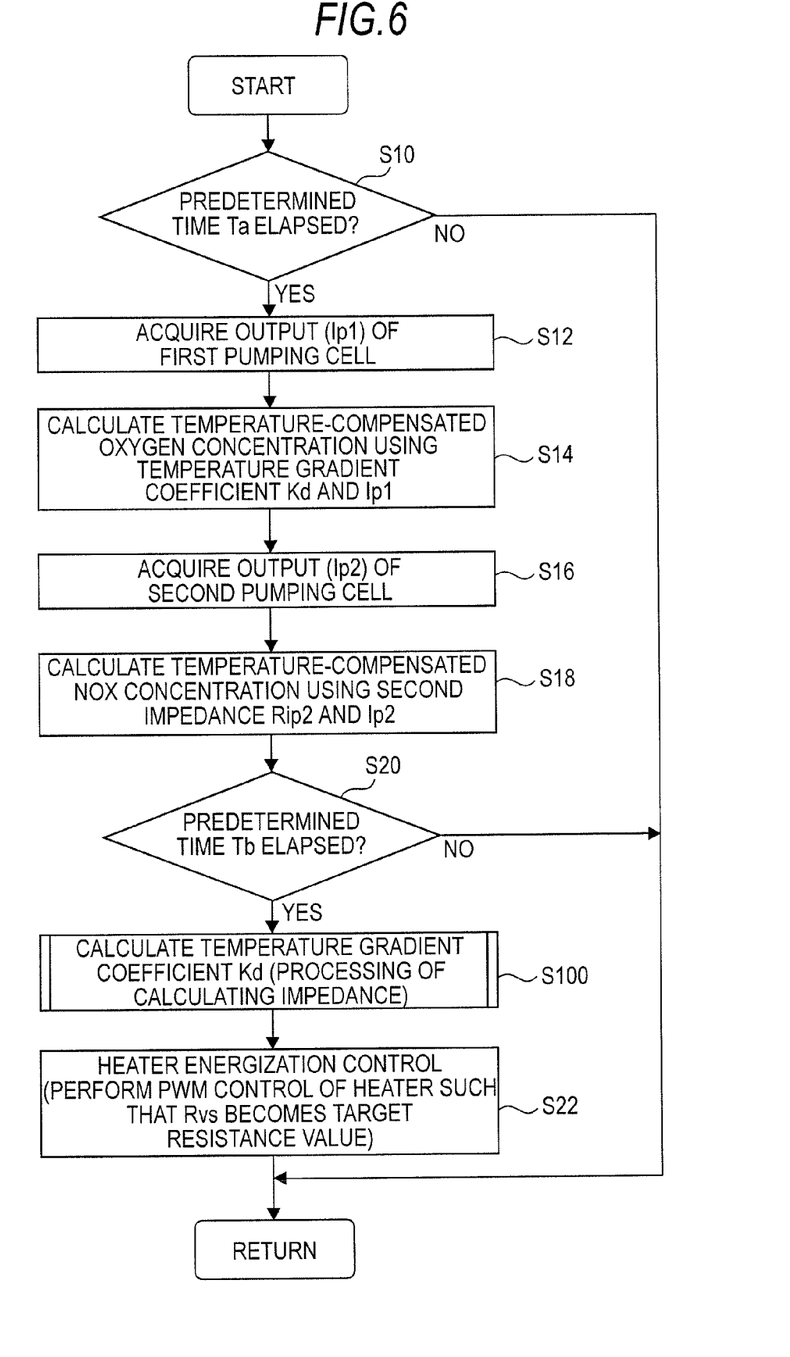
FIG. 6 is a view showing the flow of a main routine of temperature compensation processing.
Figure 7:
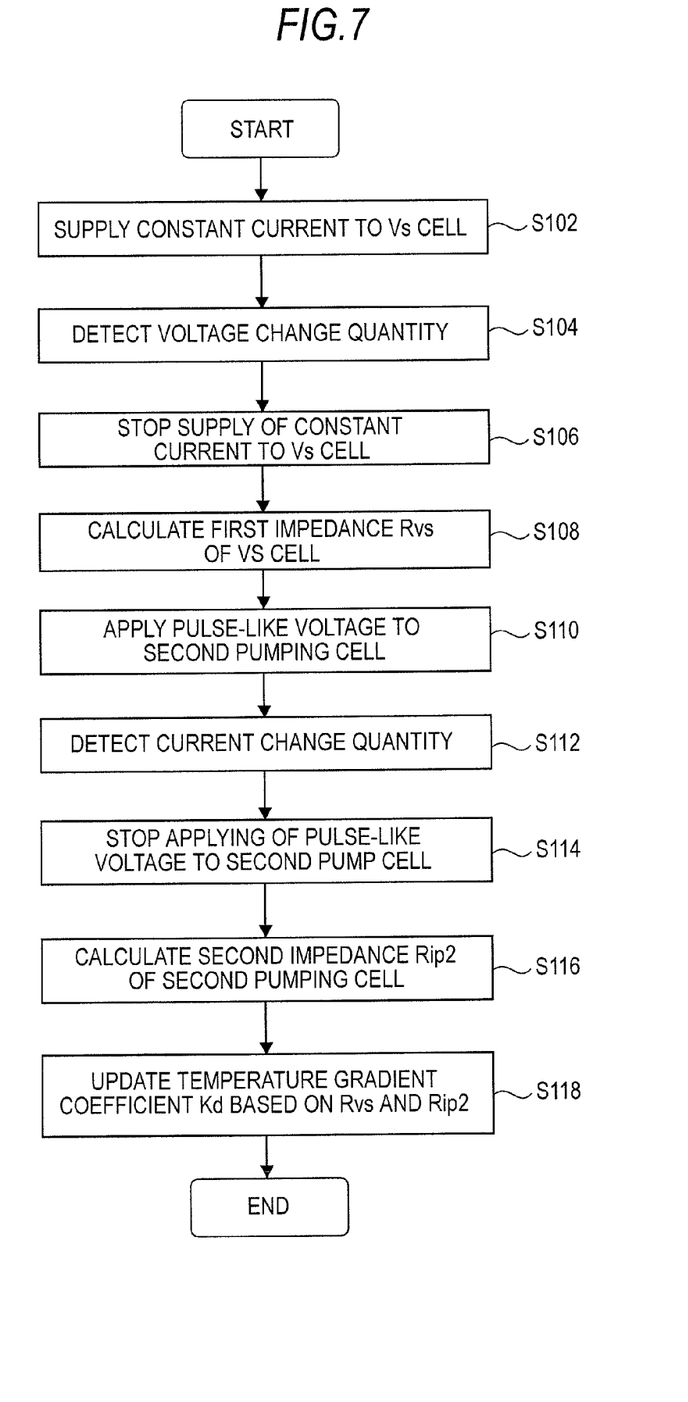
FIG. 7 is a view showing the flow of a subroutine called in the main routine shown in FIG. 6.

Next, the flow of temperature compensation processing is explained in conjunction with FIG. 6 and FIG. 7. FIG. 6 shows a main routine of the temperature compensation processing and FIG. 7 shows a sub routine which is called in the main routine.

In FIG. 6, the CPU 61 waits for timing for executing processing in the main routine until a predetermined time Ta elapses (step S10). When the determination in step S10 is "Yes", the processing advances to step S12 where the CPU 61 acquires an output (first pumping current) Ip1 of the first pumping cell 110. On the other hand, when the determination in step S10 is "No", the processing returns to the initial step of the main routine.

Next, the CPU 61 calculates the oxygen concentration in a gas to be measured using the temperature gradient coefficient Kd explained in conjunction with FIG. 3 and the Ip1 obtained in step S12 (step S14). Here, an initial value Kdf of the temperature gradient coefficient is stored in the ROM 63 in advance. When the NOx sensor control apparatus 1 is started, the initial value Kdf is read in step S14 and, hereinafter, the temperature gradient coefficient Kd is updated in the sub routine. In step S14, the CPU 61 reads the temperature gradient coefficient Kd(Kdf) and, thereafter, calculates a temperature compensation quantity Tco based on Kd(Kdf) and ΔXs1, and calculates a current value which is obtained by adding information on the temperature compensation quantity Tco to a first pumping current Ip1 detected via the Ip1 drive circuit 52 (corrected current value) as a true value (a value determined by taking into account a change in a temperature of the first pumping current). Then, the CPU 61 calculates the temperature-compensated oxygen concentration in a gas to be measured based on the true value. A quantity of change in the first pumping current Ip1 which corresponds to the temperature compensation quantity TCO may be stored as a map or may be set as a relational formula (arithmetic operational formula) between the first pumping current Ip1 and the temperature compensation quantity Tco.

Next, the CPU 61 acquires an output (second pumping current) Ip2 of the second pumping cell 130 (step S16). Then, the CPU 61 calculates the NOx concentration using the latest second impedance Rip2 which is calculated in step S116 executed in the sub routine described later and the second pumping current Ip2 acquired in step S16 (step S18). That is, in step S18, the CPU 61 calculates a current value which is obtained by adding information on the latest second impedance Rip2 to the second pumping current Ip2 (corrected current value) as a true value. Then, the CPU 61 calculates the temperature-compensated NOx concentration based on the true value. A quantity of change in the second pumping current Ip2 which corresponds to the second impedance Rip2 may be stored as a map or may be set as a relational formula (arithmetic operational formula) between the second pumping current Ip2 and the second impedance Rip2.

Next, the CPU 61 waits for timing for executing calculation (updating) of a temperature gradient coefficient Kd until a predetermined time Tb elapses (step S20). When the determination in step S20 is "Yes", the processing advances to step S100 where the CPU 61 executes processing of calculating a temperature gradient coefficient Kd (see FIG. 7). On the other hand, when the determination in step S20 is "No", the processing returns to the initial step of the main routine.

Then, when the processing of calculating the temperature gradient coefficient Kd in step S100 is finished, the CPU 61 executes an energization control of the heater 164 based on the first impedance Rvs of the oxygen concentration detection cell 120 as described above (step S22) and the processing returns to the initial step of the main routine.

As described above, with the use of the temperature gradient coefficient Kd, the temperature gradient of the NOx sensor element in the axis O direction can be cancelled so that the accurate oxygen concentration in a gas to be measured which reflects the temperature of the first pumping cell 110 can be calculated (step S14).

Next, the flow of the processing of calculating a temperature gradient coefficient Kd which is the sub routine is explained in conjunction with FIG. 7.

Firstly, in response to an instruction from the CPU 61, the Rvs detection circuit 59a supplies a constant current to the oxygen concentration detection cell (Vs cell) 120 (step S102) and detects a voltage change quantity of the oxygen concentration detection cell 120 at this point of time (step S104). Then, the Rvs detection circuit 59a stops the supply of the constant current to the oxygen concentration detection cell 120 (step S106) and calculates the first impedance Rvs of the oxygen concentration detection cell 120 based on the above-mentioned voltage change quantity (step S108).

Further, in response to an instruction from the CPU 61, the Rip2 detection circuit 59b supplies a pulse-like voltage to the second pumping cell 130 (step S110) and detects a current change quantity of the second pumping cell 130 at this point of time (step S112). Next, the Rip2 detection circuit 59b stops the supply of a pulse-like voltage to the second pumping cell 130 (step S114) and calculates the second impedance Rip2 of the second pumping cell 130 based on the above-mentioned current change quantity (step S116).

Then, the CPU 61 obtains Ts and T2 based on Rvs and Rip2, calculates the temperature gradient coefficient Kd(= (Ts−T2)/ΔXs2) and updates a temperature gradient coefficient stored in the ROM 63 (step S118). In this manner, according to this embodiment, the CPU 61 updates the temperature gradient coefficient Kd necessary for calculating the oxygen concentration in a gas to be measured at any time in step S14.

Figure 8:
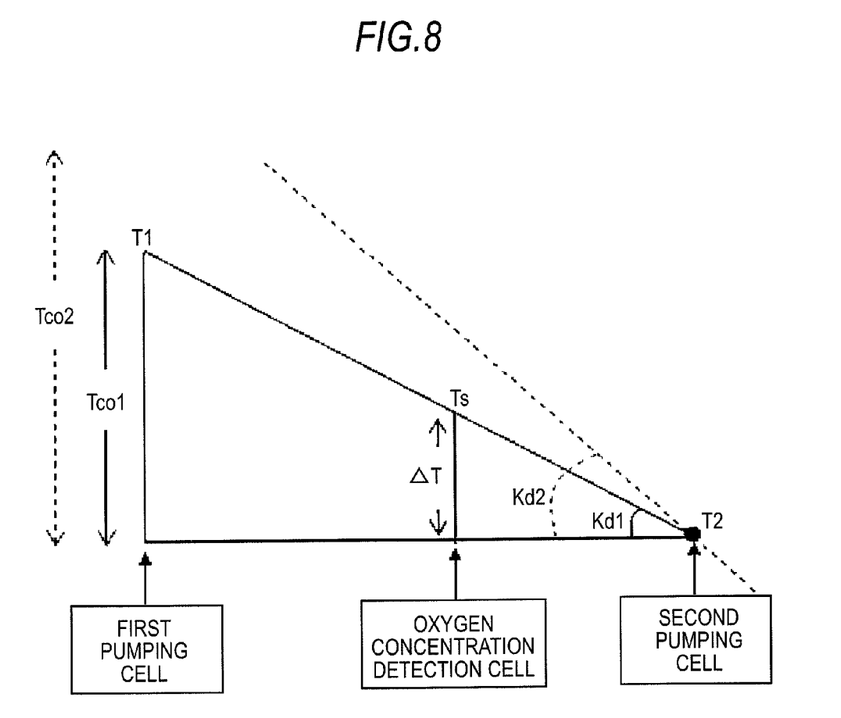
FIG. 8 is a view showing a method for calculating Kd and Tco when a temperature of the second pumping cell is controlled to a target temperature.

It is needless to say that the present invention is not limited to the above-mentioned embodiment and embraces various modifications and equivalents which are included in the technical concept and the scope of the present invention. For example, in the above-mentioned embodiment, the temperature of the oxygen concentration detection cell 120 is controlled to the target temperature using the heater 164. However, the temperature of the first pumping cell 110 or the temperature of the second pumping cell 130 may be controlled to the target temperature by the heater 164. That is, either of the first pumping cell 110 and the second pumping cell 130 may be set as "first cell" of the present invention, and either one of the remaining two cells may be set as "second cell" and the other of the remaining two cells may be set as "third cell". FIG. 8 shows the relationship between the temperature gradient coefficient Kd and the temperature compensation quantity Tco (calculation method) when the temperature of the second pumping cell 130 is controlled to the target temperature by the heater 164. In the example shown in FIG. 8, the cell temperature T2 of the second pumping cell 130 is held at a substantially fixed value even when an external temperature is changed, and the first pumping current Ip1 of the first pumping cell 110 is corrected using the temperature gradient coefficient Kd calculated based on such relationship.

Further, in the above-mentioned embodiment, the temperature gradient coefficient Kd(=(Ts−T2)/ΔXs2) is measured to obtain the temperature compensation quantity Tco. However, provided that a parameter reflects a change in temperature between Ts and T2, the parameter is not limited to the temperature gradient coefficient Kd, and the deviation between the first impedance Rvs and the second impedance Rip2 may be directly used, for example.

Further, in the above-mentioned embodiment, the correction of the second pumping current Ip2 is performed by using the latest second impedance Rip2. However, in the same manner as the correction of the first pumping current Ip1, the correction of the second pumping current Ip2 may be performed using the temperature gradient coefficient Kd calculated in step S118 so that the temperature compensation of the current Ip2 is performed and the NOx concentration is calculated.

Description of Reference Numerals and Signs

1: NOx sensor control apparatus
10: NOx sensor
57, 60: heater control means (heater energizing circuit, micon)
59a, 60: first impedance detection means (Rvs detection circuit and micon)
59b, 60: second impedance detection means (Rip2 detection circuit and micon)
60: output correction means (micon)
100: NOx sensor element
110: first pumping cell
120: second pumping cell
130: oxygen concentration detection cell
111, 121, 131: solid electrolyte
150: first measuring chamber
160: NOx measuring chamber
164: heater
O: axis

The invention claimed is:

1. A NOx sensor control apparatus which is connected to a NOx sensor, the NOx sensor having a NOx sensor element which comprises: an oxygen concentration detection cell which has an oxygen ion conductive solid electrolyte and a pair of electrodes, and generates an output corresponding to oxygen concentration in a gas to be measured which is introduced into a first measuring chamber; a first pumping cell which has an oxygen ion conductive solid electrolyte and a pair of electrodes, adjusts oxygen concentration in the first measuring chamber by pumping out or pumping in oxygen in the gas to be measured which is introduced into the first measuring chamber such that the output of the oxygen concentration detection cell becomes a predetermined value, and allows an output corresponding to the oxygen concentration in the gas to be measured; a second pumping cell which has an oxygen ion conductive solid electrolyte and a pair of electrodes, and allows a pumping current corresponding to NOx concentration in the gas to be measured which flows into the NOx measuring chamber from the first measuring chamber and has oxygen concentration thereof adjusted to flow therein; and a heater, the first pumping cell, the oxygen concentration detection cell and the second pumping cell are sequentially arranged from a distal end side along the axial direction of the NOx sensor element, the NOx sensor control apparatus comprising:

a first impedance detection means which detects first impedance of a first cell which is constituted of one of the oxygen concentration detection cell, the first pumping cell and the second pumping cell;

a heater control means which performs an energization control of the heater such that the first impedance of the first cell becomes a target value;

a second impedance detection means which detects second impedance of a second cell which is constituted of one of the oxygen concentration detection cell, the first pumping cell and the second pumping cell, and differs from the first cell; and an output correction means which corrects at least an output of a third cell which differs from the first cell and the second cell based on the deviation between the first impedance and the second impedance.

2. The NOx sensor control apparatus according to claim 1, wherein the first cell is the oxygen concentration detection cell.

3. The NOx sensor control apparatus as claimed in claim 1, wherein the output correction means calculates a temperature gradient coefficient between the first cell and the second cell using the deviation, and corrects the output of the third cell using the temperature gradient coefficient.

* * * * *